United States Patent [19]

Demi

[11] Patent Number: 4,513,741

[45] Date of Patent: Apr. 30, 1985

[54] APPARATUS ADAPTABLE FOR TREATING ANIMALS

[76] Inventor: Roy C. Demi, 736 Melvin Dr., Greensburg, Pa. 15601

[21] Appl. No.: 466,070

[22] Filed: Feb. 14, 1983

[51] Int. Cl.[3] .......... A61M 16/00

[52] U.S. Cl. .......... 128/205.25; 128/206.21; 128/206.26; 128/206.29

[58] Field of Search .......... 128/203.29, 205.25, 128/206.21, 206.26, 206.29, 207.12, 207.14, 207.16, 205.13, 205.18, 205.16, 206.24, 201.23

[56] References Cited

U.S. PATENT DOCUMENTS

| | | | |
|---|---|---|---|
| 1,105,127 | 7/1914 | Drager | 128/206.26 |
| 1,848,234 | 3/1932 | Swope et al. | 128/205.25 |
| 2,843,119 | 7/1958 | Glasser | 128/205.25 |
| 3,628,532 | 12/1971 | Magrath | 128/207.16 |

FOREIGN PATENT DOCUMENTS

| | | | |
|---|---|---|---|
| 3000518 | 7/1981 | Fed. Rep. of Germany | 128/203.29 |
| 336052 | 2/1904 | France | 128/201.23 |

*Primary Examiner*—Henry J. Recla
*Attorney, Agent, or Firm*—Harold W. Adams

[57] ABSTRACT

Apparatus for treating animals including a muzzle, a muzzle pump assembly, a respiratory valve assembly and a respirator pump assembly. The units may be selectively assembled to serve as a pneumatic muzzle, a respirator for administering air, oxygen and other gases and to inject medicants, all of which operations may be performed when the treated animal is within its parent.

20 Claims, 11 Drawing Figures

APPARATUS ADAPTABLE FOR TREATING ANIMALS

BACKGROUND OF THE INVENTION

Respiratory and treatment apparatus for animals having elongated snouts such as horses, cows, sheep, dogs and other such domesticated and wild animals are generally known. For instance, see U.S. Pat. Nos. 2,843,119; 3,915,165; 2,960,886; and 3,628,532 for some typical prior art devices.

As seen, conventional animal respirators include tanks and valves for supplying oxygen and medicants and relatively large and bulky muzzles for covering the animal's mouth and nostrils. Typically a halter is used to secure the muzzle over the animal's snout though Glasser (U.S. Pat. No. 2,843,119—supra) discloses the use of an inflatable ring or cuff that is connected to a separate air supply through a tire valve. The ring in this instance is used only for the purpose of effecting a seal and not in a muzzle.

Another disadvantage of such prior art devices is that because of their design and size, none are adaptable to serve a principal purpose of this invention—to save malpositioned offspring from suffocation within the parent during birth. That happens frequently enough so that it is a costly limitation to those engaged in producing registered livestock and rare animals such as horse and cattle breeders and zookeepers.

SUMMARY OF THE INVENTION

An object of this invention is to provide an animal treatment apparatus for supplying air to an animal within the parent as required during its birth.

Another object of the invention is to provide an animal treatment apparatus that includes a flexible, pneumatic muzzle that may be secured to the snout of an animal while it is within the parent during the animal's birth and a respirator pump for administering air or oxygen to the animal through said muzzle.

Still another object of the invention is to provide a flexible, pneumatic muzzle having an inflatable cuff and an inflatable mouthpiece, the cuff and mouthpiece cooperating to secure the muzzle to the animal's snout when inflated.

Yet another object of the invention is to provide the foregoing muzzle with a muzzle pump for inflating the said cuff and mouthpiece.

A further object of the invention is to provide an animal treatment apparatus that includes a pneumatic muzzle having an inflatable cuff and a mouthpiece, the cuff and mouthpiece cooperating to secure the muzzle to the elongated snout of an animal being treated when the cuff is inflated. A passage is provided in the mouthpiece for administering medication internally.

DESCRIPTION OF THE DRAWINGS

The foregoing and other objects and advantages of the invention will become apparent when read in light of the appended drawings wherein:

Referring to FIGS. 1-3, a preferred embodiment of the invention is shown as including a muzzle generally designated by the reference numeral 10 and a muzzle pump generally designated by the reference numeral 46. The muzzle includes a flexible, bell-shaped bag 11 having an open-mouth 12 at the large end 13 and a bore 14 at the smaller end 15. The bag 11 may be formed of a scrubbable fabric reinforced on both sides with rubber. The smaller end 15 is captured between an inner circular end plate 16 and an outer flange 17 on a connector plug 18 to form an open, interior chamber 19 in the bag 11.

Figure 1:
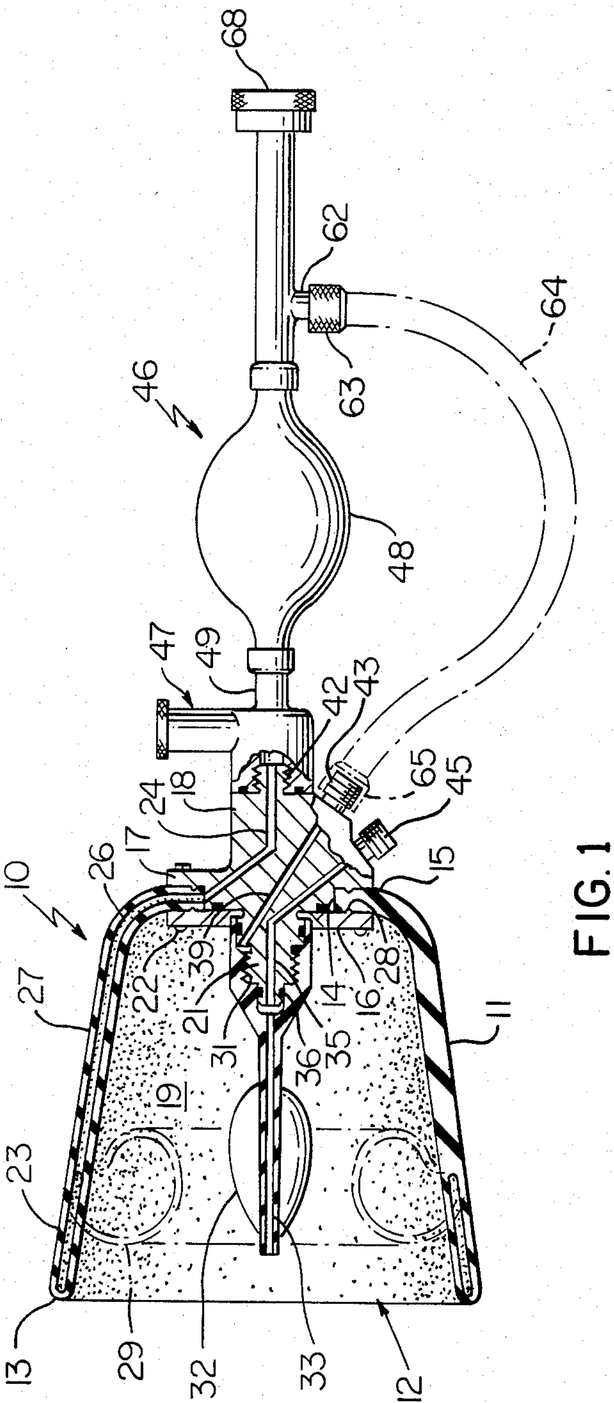
FIG. 1 is a side elevational view in partial section of a preferred embodiment of a pneumatic muzzle and muzzle pump in accordance with the principles of the invention.

The bore 14 receives the threaded end 21 of the plug 18, the plug 18 being rigidly secured to the end 15 of the bag 11 by means of suitable bolts or other fasteners 22 spaced around the circumference of the end plate 16, the fasteners 22 passing through the end plate 16 and flange 17. Radial sealing beads 28 assure a gas-tight assembly between the bore 24 and first passage 26.

The open end 12 of the bag 11 is arranged with an internal, closed and continuous first pressure chamber 23 that extends around the open end 12 of the bag 11. The first pressure chamber 23 is connected to a bore 24 in the plug 18 by means of a first passage 26 integrally formed in the sidewall 27 of the bag 11.

When the first passage 26 is connected to an air supply the first pressure chamber 23 is inflated causing the sidewall 27 forming the chamber 23 to expand and turn inwardly to form an inflated cuff 29 as shown in dotted lines in FIG. 1.

The threaded end 21 of the plug 18 mates with the female thread 31 of a solid rubber mouthpiece 32 provided with a through-bore 33 that communicates with a bore 35 in the plug 18. A seal 36 assures a gas-tight connection. The mouthpiece 32 is formed of a sterilizable rubber or the like and shaped to generally conform to the interior of the animal's mouth when inserted past its gums and teeth.

Figure 2:
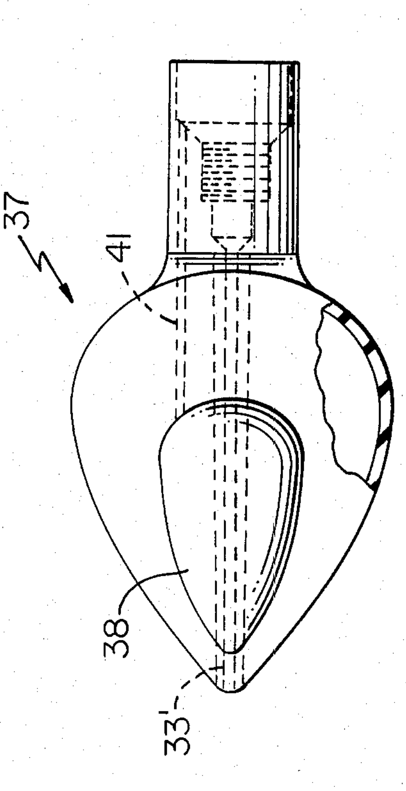
FIG. 2 is a plan view of an inflatable mouthpiece used with the invention.

An inflatable mouthpiece generally designated by the reference number 37 as shown in FIG. 2 may be used in place of the solid mouthpiece 32. The mouthpiece 37 is formed of a flexible rubber material and includes a through-bore 33' that communicates with the bore 35 in the plug 18 when the threaded end 21 mates with the female thread 31'. The mouthpiece 37 includes a second pressure chamber 38 that is connected to a bore 39 in plug 18 by means of a second passage 41. The bores 24, 35 and 39 are brought out of the plug 18 through threaded ports 42, 45 and 43 respectively.

Figure 3:
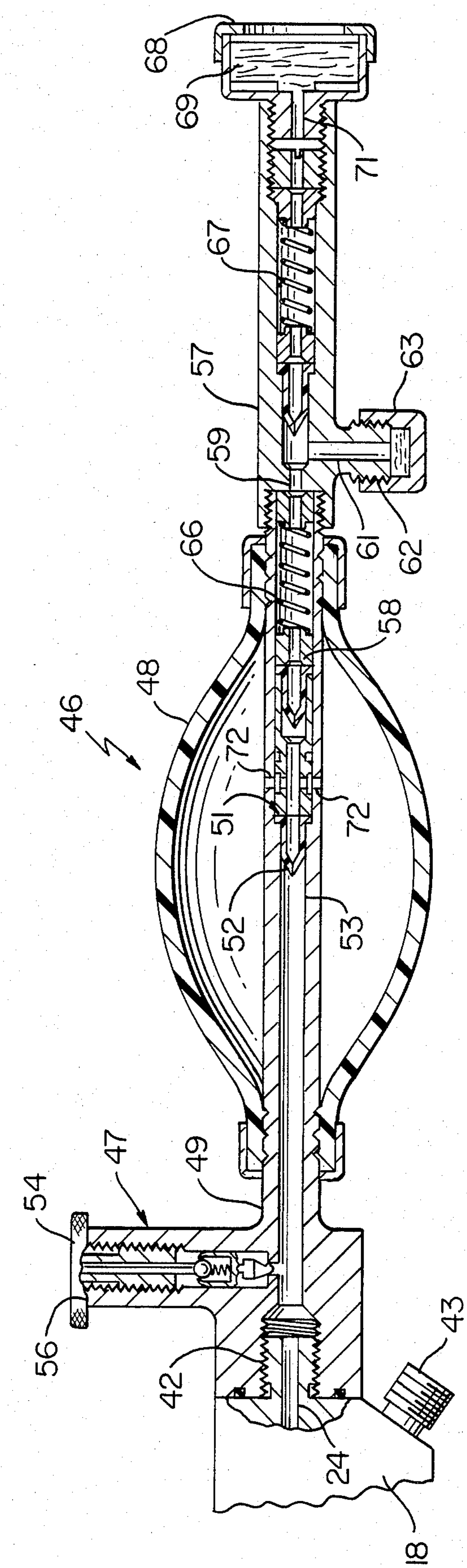
FIG. 3 is a partial cross-sectional view illustrating the muzzle pump in greater detail.

As shown in FIG. 3 the air pressure required to inflate both the inflatable cuff 29 and mouthpiece 37 is provided by the muzzle air pump generally designated by reference numeral 46. The muzzle pump 46 includes an "on-off" needle valve 47 and a squeeze-bulb 48 surrounding a main, stainless steel tubular body section 49 that provides a first pump output pressure stage 51.

The output pressure stage 51 is connected by means of a check valve 52 to a central passage 53 that opens into the bore 24 of plug 18. The pump 46 is threadably connected to the port 42 of the plug 18. Thus the pressure output from the first pump stage 51 is connected to the first pressure chamber 23 to inflate the inflatable cuff 29.

The "on-off" needle valve 47 connects the central passage 53 to atmosphere when open or "Off" to exhaust the pressure in the inflatable cuff 29. The operation and structure of the needle valve 47, which is commercially available, are well-known and need not be described in detail. In the arrangement shown, clockwise rotation of the cap 54 until it seats on shoulder 56 closes the needle valve 47 turning it "on". Rotation counter-clockwise turns the needle valve 47 "off".

An auxilliary pump body section 57 provides a second output stage 58 which is connected to a second central passage 59. A bore 61 from passage 59 extends through a threaded port 62 that may be closed by means of a threaded cap 63 when the solid mouthpiece 32 is used.

When the inflated mouthpiece 37 is used, the ports 62 and 43 are connected by means of a flexible tube 64 as shown in dotted lines in FIG. 1. In this event, port 45 is closed with a cap 63.

The main body section 49 and the axuilliary body section 57 include a spring-loaded check valve 66 and 67 respectively. Check valve 66 interconnects central passages 53 and 59. Check valve 67 interconnects the central passage 59 to an exhaust outlet 68 that includes a filter 69 by means of a bore 71.

To explain the operation of the pnuematic muzzle 10 just described, assume it is desired to administer medication to an animal with an elongated snout such as a foal. The flexible bag 11 is placed over foal's snout and the mouthpiece 32 inserted into its mouth beyond the teeth and gums. Holding the positioned muzzle in place with one hand, the bulb 48 is repeatedly squeezed and released with the other hand. The ports 43 and 62 are closed and the port 45 connected to a supply of medication to be supplied under pressure or by gravity by a tubing not shown. The needle valve 47 is turned to the "on" position.

Each time the bulb 48 is squeezed, the air inside the bulb is forced into central passage 53 through openings 72 and out the check valve 52 into the first pressure chamber 23 to inflate the cuff 29. Release of the bulb 48 closes the check valve 52. The bulb 48, due to its residual memory imparted by its molding, returns to its original shape. The interior of the bulb is again at atmospheric pressure, air returning therein through the exhaust outlet 68, bore 71, check valves 67 and 66, central passages 58 and 59 and openings 72.

This squeeze and release cycle is repeated until the pressure in the inflatable cuff 29 (first pressure stage) overcomes the resistance of the spring check valve 66 to connect the central passages 53 and 59. Continued pump action increases the second stage air pressure until the spring-loaded check valve 67 opens connecting the passage 59 to the exhaust outlet 68. When a solid mouthpiece 32 is used, the spring-loaded check valves 66 and 67 may be adjusted so that the output air pressure of the first and second stages are equal.

As the cuff 29 inflates it expands inwardly gripping the animal's snout and forming a substantially sealed chamber 19 inside the bag. This gripping force binds the animal's jaws together over the enlarged end of the mouthpiece 32 preventing its withdrawal. Thus the inflatable cuff 29 and mouthpiece 32 cooperate when the cuff is inflated to secure the muzzle 10 to the animal's snout.

The stainless steel body section 49 provides sufficient strength so that the bulb surrounding it may serve as a handle with which to lead the muzzled animal. Medication is administered through the port 45 and bore 33. In the event the inflatable mouthpiece 37 is used the ports 43 and 62 are connected by means of the flexible tubing 64 and a cap 63 placed on port 45. The spring-loaded check valves 66 and 67 are adjusted to open in sequence at increasingly greater output pressures. Thus the cuff 29 is inflated first to a pressure determined by the spring-loaded check valve 66 before the mouthpiece 37 is inflated to a second higher pressure which is maintained by the spring-loaded check valve 67.

FIGS. 4–7 disclose a muzzle 10' and the muzzle pump 46 being used with a preferred respiratory valve assembly generally designated by the reference numeral 74. The muzzle 10' is the same as the muzzle 10 except for a redesigned connector plug 18' which includes inlet and outlet bores 75 and 76 that open through the end plate 16' into the chamber 19'. A solid mouthpiece 32 or an inflatable mouthpiece 37 may be used as previously described.

Figure 7:
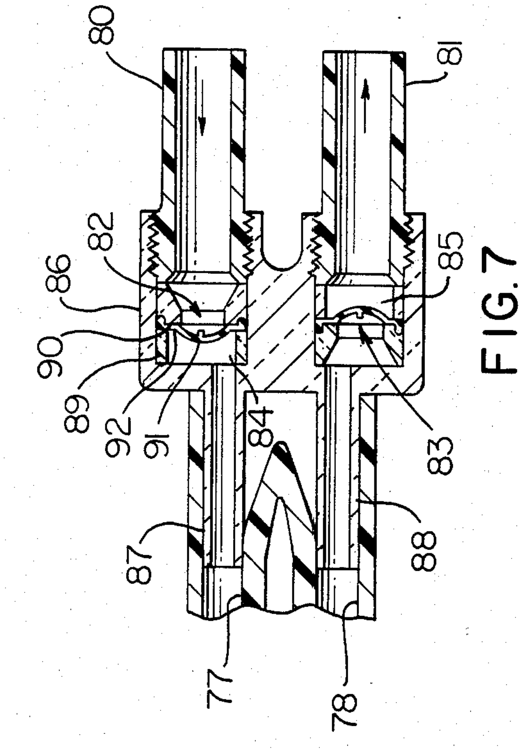
FIG. 7 is a sectional view taken along the lines 7—7 in FIG. 4 illustrating a preferred embodiment of a respiratory valve assembly used with the muzzle.

The inlet and outlet bores 75 and 76 open into inlet and outlet passages 77 and 78 respectively in a flexible conduit 79 clamped to the end plug 18. The passages 77 and 78 are connected to inlet and outlet ports 80 and 81 through inlet and outlet flapper valves 82 and 83 (FIG. 7). The inlet and outlet flapper valves 82 and 83 are mounted in chambers 84 and 85 in a valve body 86 provided with tubular male couplings 87 and 88 that sealingly project into the inlet and outlet passages 77 and 78 respectively. Chambers 84 and 85 are each provided with a spacer 89 and a valve seat 90 held in a compression by the inlet and outlet ports 81 and 82 which are threadably received within the valve body 86.

The identical inlet and outlet flapper valves 82 and 83 are commercially available and their operation well-known. In the case of inlet flapper valve 82, a small, arcuate portion of a domed valve member 91 is attached to the valve seat 90 by means of an integral hinge or web 92. This permits the normally closed valve member 91 to move off the valve seat 90 into the chamber 84 when there is gas or air under pressure connected to the inlet port 80 or a suction or pressure drop occurs as during inhalation by the muzzled animal. Opening of the inlet flapper valve 82 thus permits air to flow into the interior chamber 19 of the bag 11'.

The outlet flapper valve 83 operates in the same fashion except in the opposite direction. The outlet flapper valve 83 opens only during exhalation by the animal or during evacuation of the interior chamber 19 of the muzzle 10'. The valve body 86 may be formed of a transparent plastic permitting the user to observe the position and movement of the respective valves 82 and 83 and thus the animal's breathing rate.

The flexible conduit 79 also includes bores 94 and 95 that open into the first and second passages 26' and 41' respectively through the bores 24' and 39' in plug 18'. The end 96 of conduit 79 is branched, one leg 97 being threadably attached to the muzzle pump 46 by means of a male plug 98 that is received in bore 94, thus connecting the bore 94 and first central passage 53. The other branch 99 is threadably mounted to the port 62, thus connecting the bore 95 and the second central passage 59 (FIG. 3).

The operation of the muzzle 10' and muzzle pump assembly 46 are the same as previously prescribed. When used with the respirator valve assembly 74 a typical operation is described as follows. Assume a foal is mal-positioned within a mare at the time of delivery and in danger of suffocation.

The flexible sterilized bag 11' is inserted by an attendant using one hand into the mare's womb and loosely positioned over the foal's mouth and nostrils, the mouthpiece 32 or 37 being pushed into the foal's mouth past the gums and any front teeth. The needle valve 47 is turned "on" and the bulb 48 squeezed and released until the cuff 29' is inflated sealingly securing the bag 11' to the animal's snout.

If a solid mouthpiece 32 is used, the port 62 may be connected to the inlet port 80 by means of a flexible tube (not shown) thus connecting the second central passage 59 and the pressure output of the second pump stage to the interior chamber 19' of the bag 11'.

Continued operation of the squeeze bulb 48 forces air under pressure through the inlet and outlet flapper valves 82 and 83 to clear the bag 11' of blood and mucous. When the cleaning operation is completed, the port 62 is capped (again only when a solid mouthpiece 32 is used). Continued operation of the pump 46 opens the check valve 67. The foal's breathing can be observed by watching the operation of the flapper valves 82 and 83 through the transparent valve body 86.

In the event the foal is unable to breathe, air or oxygen may be forcefully administered to assist respiration. A respirator pump generally designated by the reference numeral 100 is provided for this purpose.

The pump body 101 is provided with a smooth bore 102 which terminates at the bottom wall 103 of the body 101. A suitable cover 104 encloses the bore 102 at its top end. The cover 104 is provided with a bore 106 concentric with the bore 102 that serves as a guide for the operating rod 107 of the piston 108. The guide is arranged with a seal 105.

Figure 9:
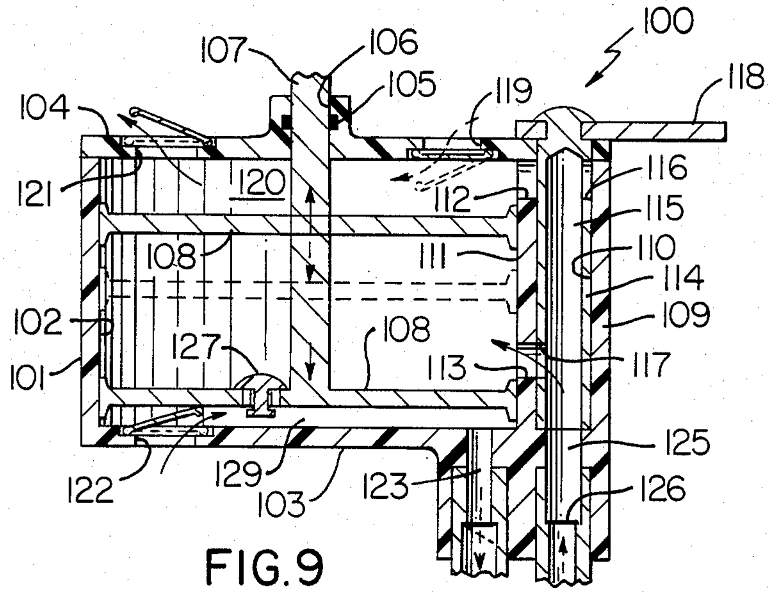
FIG. 9 is a partial cross-sectional view illustrating the respiratory pump in a respiration mode of operation.
Figure 11:
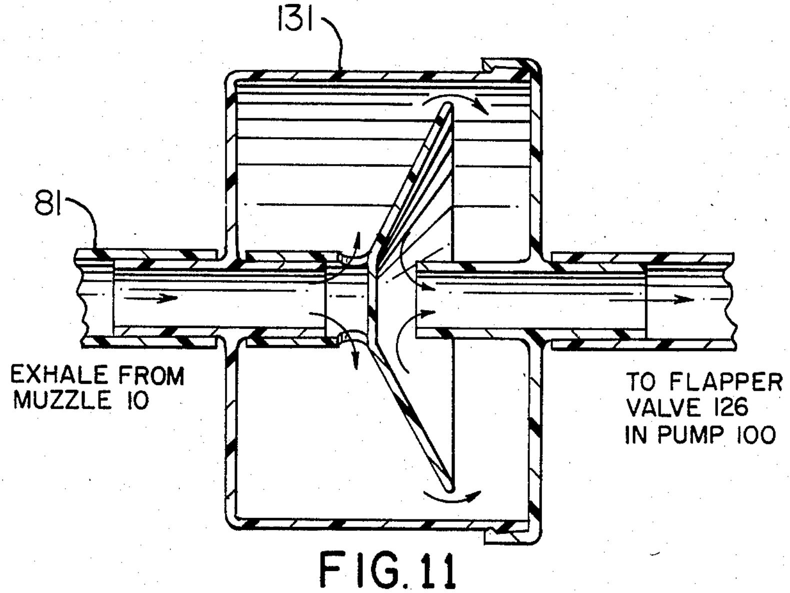
FIG. 11 is a sectional view of a trap connected between the respiratory valve assembly and the respiratory pump.

The bore 102 also includes an integral valve housing 109 which is provided with a bore 110 that is parallel to the bore 102 and separated by the common wall section 111. The bores 102 and 110 are provided with communicating ports 112 upper and 113 lower as shown in FIG. 9.

The bore 110 is arranged with a rotary valve member 114 having a neat fit on the diameters. The valve 114 is provided with a hollowed chamber 115 and two ports 116 and 117 at opposite ends and opposed to each other but communicating alternately with ports 112 and 113 in 180° arc positions. The closed end of the valve 114 is arranged with another rotary valve member 118 having an accurate portion and fixed to the valve member when the ports 113 and 117 communicate with each other. Therefore, when the valve 114 is rotated 180°, the valve member 118 closes the port 119. Only ports 112 and 116 will be in communication. The closed cylinder 120 is arranged with three ports 119, 121 and 122 arranged with flapper check valves. In the cover, port 119 is an inlet and port 121 is an outlet. Port 122 is located in the bottom wall and serves as an inlet port. The bottom wall also includes an open port 123 that is parallel to the port 125 that opens into the chamber 115 of the valve 114.

Ports 123 and 125 are arranged to mate and connect to the valve body 86 of the respirator valve 74. Thus inlet and outlet ports 80 and 81 open into passages 123 and 125 respectively. The piston 108 is arranged with a relief valve 127 that limits the pressure that can be reached in the chamber 129.

Figure 8:
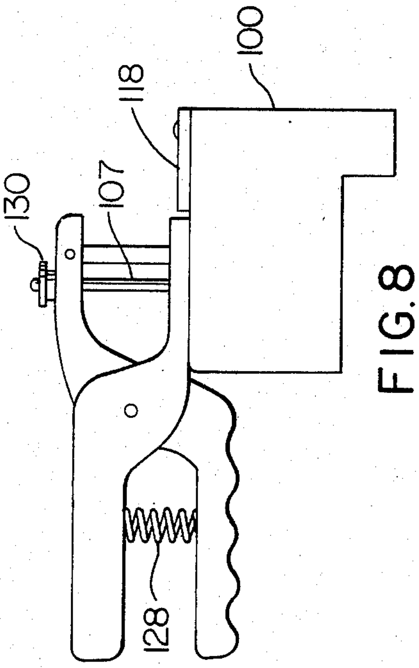
FIG. 8 is a side view of a preferred embodiment of a respiratory pump used with the respiratory valve assembly.
Figures 4, 5, 6:
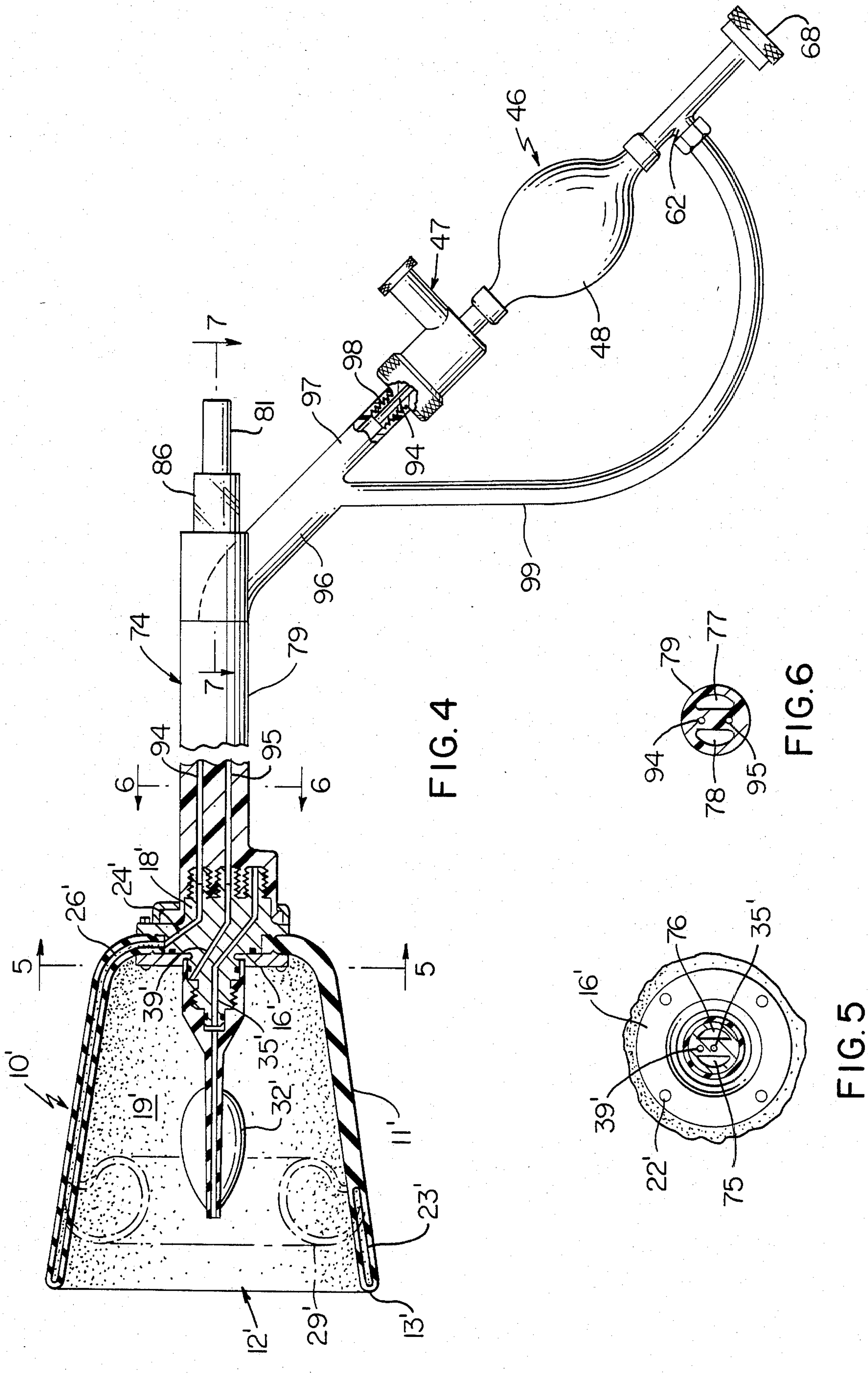
FIG. 4 is a side-elevational view in partial section illustrating a respiratory valve assembly used with the invention.
FIG. 5 is a sectional view taken along the lines 5—5 in FIG. 4 illustrating inlet and outlet bores in the muzzle.
FIG. 6 is a cross-sectional view taken along the lines 6—6 in FIG. 4 illustrating inlet and outlet passages in a conduit connected to the muzzle.

The pump 100 is actuated by the lever arrangement shown in FIG. 8. One lever is rigidly secured to the pump lever and the other is pivotally attached to the piston rod 107. A return spring 128 returns the piston to its starting up position after the levers are manually squeezed and released. An adjustable stop 130 limits the length of stroke of the pump 100 and thus the volume of gas displaced with each stroke.

A conventional trap 131 is included in the line between the outlet 81 of the respirator valve assembly 74 and the flapper valve 126 in the respirator pump 100 to catch any blood and mucous evacuated from the chamber 19 in the muzzle 10. It is understood that valve 126 and valve 83 are the same when the respiratory pump 100 is used with the respiratory valve assembly 74.

Figure 10:
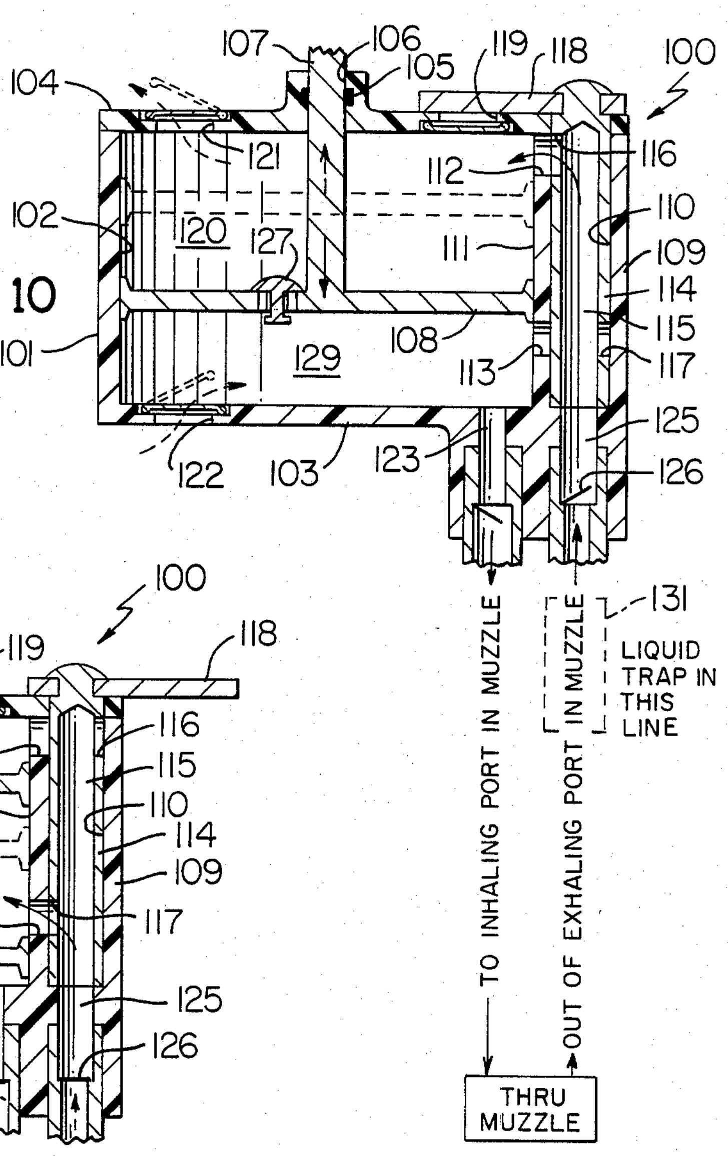
FIG. 10 is a partial cross-sectional view illustrating the respiratory pump in an evacuation mode of operation.

In operation, after the muzzle 10 is secured to the foal's snout, the respirator pump 100 is first used to remove the blood and mucous from within the bag 11 by placing the selector valve member in the evacuation position as shown in FIG. 10. The pump levers are squeezed slowly, the downward stroke of piston 108 pushing air from the chamber 129 through flapper valve 82, into the chamber 19, valve 83, trap 131, valve 126 and port 112 into chamber 120.

Release of the levers returns the piston 108 to its upper starting position. Port 122 opens taking fresh air into the chamber 129. Ports 119, 121 and 113 and valve 82 are closed. Port 112 is open. Pressure in chamber 120 opens port 121 to exhaust air to the atmosphere.

To forcefully administer air or other gases, the selector valve member 118 is rotated to the position shown in FIG. 9 placing the pump 100 in the respiration mode of operation. The levers are again squeezed slowly, the ports 121 and 112 being closed and ports 113 and 119 open to refill the chamber 120. The air in chamber 129 is pushed through the valve 82. Since port 112 is closed, the pressure within the chamber 19 inflates the foal's lungs with fresh air to complete an inhalation cycle.

When the piston 108 passes port 113 the valve 83 opens and air exhausts behind the piston 108 into the chamber 120. This closes port 119 and opens 121 to exhaust the used air to atmosphere in an exhalation cycle.

When the levers are released, the port 121 remains open to exhaust air in the chamber 120 to atmosphere and port 122 opens to take fresh air into the chamber 129. Ports 119 and 112 are closed. Valve 82 closes. Valve 113 remains closed after the piston 108 returns past port 113 because it is a higher force valve than the valve at port 122. Continued return of the piston 108 pushes the exhaled air through the port 121 to the atmosphere.

When the foal being administered to commences breathing on its own, the respiratory pump 100 is disconnected from the respiratory valve 74. The animal's breathing rate may be observed through the transparent valve body 86. The muzzle 10 is left in place over the animal's snout until the foal can be safely removed from the mare.

While described for use in the delivery of mal-positioned off-spring, the afore-described invention has numerous other uses and applications in the treatment of animals and is to be limited only by the scope of the appended claims.

I claim:

1. Apparatus adaptable for treating animals comprising:

muzzle means adapted to fit around the snout of an animal and formed of a flexible bag open at one end and having an aperture in the other end, plug means fitted in said aperture and having first, second and third bores therein;

an inflatable cuff having a first pressure chamber therein connected to and extending around said open end of said flexible bag;

a first passageway formed in said flexible bag interconnecting said first pressure chamber and said first bore in said plug means;

a mouthpiece attached to said plug means and extending into said flexible bag;

a muzzle pump and conduit means connecting said muzzle pump to said plug means and having a first passage communicating with said first bore in said plug means for pressuring said first closed chamber to inflate said inflatable cuff, said cuff and said mouthpiece cooperating to secure said muzzle means to said snout when said mouthpiece is inserted into said animal's mouth and said cuff is inflated;

said conduit means further including inlet and outlet passages communicating with said second and third bores in said plug means said second and third bores communicating with the interior of said flexible bag; and a respiratory valve positioned in each of said inlet and outlet passages, said respiratory valve in said inlet passage acting as an inhalation valve and said respiratory valve in said outlet passage acting as an exhalation valve through which said animal may breathe normally.

2. The muzzle as defined in claim 1 wherein said mouthpiece is inflatable including a second pressure chamber therein and a flow passage communicating therewith, said plug means having a fourth bore therein communicating with said flow passage; and a second passage in said conduit means communicating with said fourth bore that communicates with said second pressure chamber for inflating said mouthpiece.

3. The muzzle as defined in claim 1 wherein said pump includes means providing first and second air pressure outputs connected to said first and second passages of said conduit means, respectively.

4. The muzzle as defined in claim 3 including an overpressure relief valve connected to said conduit means between said pump and said first chamber.

5. The muzzle as defined in claim 3 wherein said first and second air pressure outputs are supplied to said first and second chambers in sequence.

6. The muzzle as defined in claim 5 including valve means for connecting said second air pressure output to atmosphere when the air pressure therein reaches a determined value.

7. The muzzle as defined in claim 1 including a passage in said mouthpiece opening into said bag.

8. The invention as defined in claim 1 wherein said respiratory valves are in a transparent valve body.

9. The invention as defined in claim 1 including respiratory pump means connected to said inlet and outlet passages for forcefully supplying air through said inhalation valve into said muzzle and exhausting air from said muzzle through said exhalation valve in a first respiratory mode of operation.

10. The invention as defined in claim 9 wherein said respiratory pump means continuously forces air through said inhalation and exhalation valves in a second evacuation mode of operation.

11. A muzzle for an animal having a snout comprising:

a flexible bag having an open end and a closed end, said open end adapted to be placed around said animal's snout, said bag having an inflatable cuff formed around said open end and adapted to grippingly engage said snout to constrict the animal's jaws from opening; and a mouthpiece connected to and extending only within said bag, said mouthpiece being shaped to generally conform to the interior cavity of the animal's mouth whereby said cuff and said mouthpiece cooperate to secure said bag to said snout when the mouthpiece is inserted into the animal's mouth and said cuff is inflated.

12. The muzzle as defined in claim 11 wherein said inflatable cuff is integrally formed on said bag.

13. The muzzle as defined in claim 11 wherein said mouthpiece is inflatable.

14. The muzzle as defined in claim 11 wherein said closed end includes an inlet and an outlet through which said animal may breathe.

15. The muzzle as defined in claim 11 wherein said mouthpiece includes passage means communicating the exterior and interior of said bag.

16. A muzzle adaptable for treating an animal comprising:

a flexible bag adapted to be fitted around an animal's snout, said bag being formed by a continuous sidewall open at one end and closed at the other;

a mouthpiece connected to said closed end and extending into said bag;

an inflatable cuff formed around said open end of said bag and having a first pressure chamber therein, said closed end having a first bore therein and a first passage in said sidewall interconnecting said first pressure chamber in said cuff and said first bore in said closed end; and a muzzle pump connected to said first bore in said closed end for pressuring said first pressure chamber to inflate said cuff, said mouthpiece and said cuff cooperating to secure said bag to said snout when said mouthpiece is inserted into the animal's mouth and said cuff is inflated.

17. The muzzle as defined in claim 16 wherein said closed end includes a second bore therein and said mouthpiece is inflatable, being formed of a flexible material defining a second pressure chamber and having a passage leading from said second bore in said closed end to said second pressure chamber therein for inflating said mouthpiece when connected to a source of fluid pressure.

18. The muzzle as defined in claim 10 wherein said muzzle pump is connected to said second bore in said closed end.

19. The muzzle as defined in claim 16 further including two passages extending through said mouthpiece and closed end, one through which the animal may inhale and one through which the animal may exhale.

20. The muzzle as defined in claim 16 wherein said mouthpiece includes a through passage that opens into said bag through said closed end.

* * * * *